United States Patent [19]

Hays et al.

[11] Patent Number: 4,733,670
[45] Date of Patent: Mar. 29, 1988

[54] DEVICE FOR CARDIAC OUTPUT MONITORING

[75] Inventors: Carl V. Hays, Barrington, Ill.; Mark Lukasiewicz, New York, N.Y.

[73] Assignee: The Kendall Company, Boston, Mass.

[21] Appl. No.: 873,602

[22] Filed: Jul. 28, 1986

Related U.S. Application Data

[63] Continuation of Ser. No. 786,445, Oct. 11, 1985, abandoned, which is a continuation of Ser. No. 586,612, Mar. 6, 1984, abandoned.

[51] Int. Cl.⁴ .............................................. A61B 5/04
[52] U.S. Cl. ................................. 128/693; 128/640; 128/734
[58] Field of Search ............... 128/639, 640, 644, 693, 128/734; 324/65 R

[56] References Cited

U.S. PATENT DOCUMENTS

| 3,340,867 | 9/1967 | Kubicek et al. | 128/734 |
| 3,835,839 | 9/1974 | Brown | 128/693 |
| 3,835,840 | 9/1974 | Mount | 128/693 |
| 3,871,359 | 3/1975 | Pacela | 128/693 |
| 3,882,851 | 5/1975 | Sigworth | 128/693 |
| 3,996,925 | 12/1976 | Djordjevich | 128/693 |
| 4,016,868 | 4/1977 | Allison | 128/644 |
| 4,116,231 | 9/1978 | Matsuo | 128/734 |
| 4,328,814 | 5/1982 | Arkans | 128/640 |
| 4,539,640 | 9/1985 | Fry et al. | 128/734 |
| 4,583,553 | 4/1986 | Shah et al. | 128/704 |

OTHER PUBLICATIONS

Sramek, "Noninvasive Technique for Measurement of Cardiac Output by Means of Electrical Impedance", Proceedings of the 5th International Conference on Electrical Bio-Impedance, Tokyo, Japan, Aug. 24–26, 1981, pp. 39–42.

Kunishige et al., "Simultaneous Recording of Impedance Pulse Wave on Ascending Aorta and Main Pulmonary Artery Branch", Proceedings of the 5th International Conference on Electrical Bio-Impedance, Tokyo, Japan, Aug. 24–26, 1981, pp. 11–12.

Primary Examiner—Kyle L. Howell
Assistant Examiner—Ruth S. Smith
Attorney, Agent, or Firm—Powell L. Sprunger; James Potthast

[57] ABSTRACT

An electrode assembly for cardiac output monitoring comprising a first pair of electrodes consisting of a first spot injection electrode for placement adjacent the xiphoid process for injecting a signal thereat and a first elongated conductive strip electrode for receipt of the signal at the xiphoid process, and a second pair of electrodes consisting of a second injection spot electrode for placement adjacent the neck for injecting a second signal thereat, a second elongated strip electrode for receipt of the second signal at the patient's neck, and a single connector assembly connected to all of the electrodes of the first and second pairs of electrodes and to a single cable connector for coupling the electrodes to a monitoring apparatus.

6 Claims, 4 Drawing Figures

U.S. Patent    Mar. 29, 1988    4,733,670
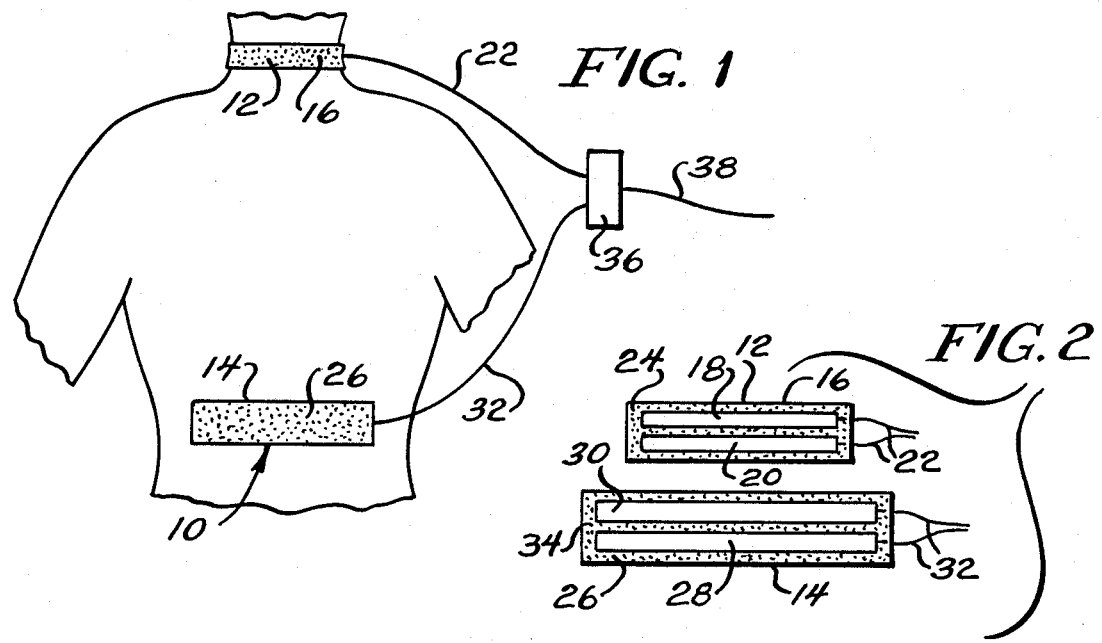
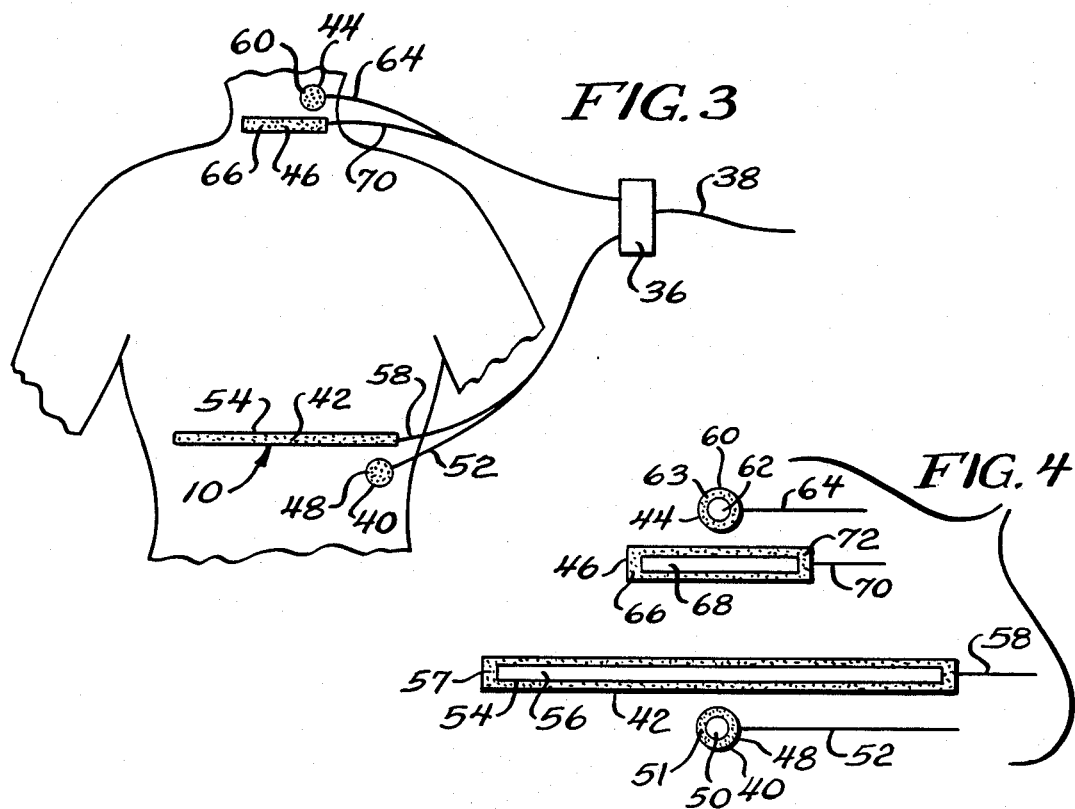

the neck, and a second elongated electrode 46 for placement adjacent the neck.

The first spot electrode 40 has a small circular backing 48, and a small circular conductive strip 50 on the backing 48. The electrode 40 has a conductive lead 52 connected to the strip 50. The electrode 40 may have adhesive 51 surrounding the strip 50 in order to secure the electrode 40 to the patient.

The first elongated electrode 42 has an elongated first backing 54, and an elongated conductive strip 56 on the backing 54. The electrode 42 has a conductive lead 58 connected to the strip 56. The electrode 42 may have adhesive 57 surrounding the strip 56 in order to secure the electrode 42 to the patient.

The second spot electrode 44 has a small circular backing 60, and a small circular conductive strip 62 on the backing 60. The electrode 44 has a conductive lead 64 connected to the strip 62. The electrode 44 may have adhesive 63 surrounding the strip 62 in order to secure the electrode 44 to the patient.

The second elongated electrode 46 has an elongated backing 66, and an elongated conductive strip 68 on the backing 66. The electrode 46 has a conductive lead 70 connected to the strip 68. The electrode 46 may have adhesive 72 surrounding the strip 68 in order to secure the electrode 46 to the patient. The backing of the electrodes 40-46 may be constructed from foam, and the conductive strips of the electrodes 40-46 may be constructed from aluminized mylar, a conductive gel, or conductive adhesive, as desired.

In use, the first spot electrode 40 is secured adjacent the xiphoid process of the patient, the first elongated electrode 42 is also secured adjacent the xiphoid process, the second spot electrode 44 is secured adjacent the neck, and the second elongated electrode 46 is secured adjacent the neck. A high frequency signal is injected into the patient's body on the first spot electrode 40, and the signal is sensed on the first elongated electrode 42. The high frequency signal is injected into the patient's body on the second spot electrode 44, and the signal is sensed on the second elongated electrode 46. The leads of the electrodes 40-46 are connected to a connector 36, and the connector 36 is connected to a monitor by leads 38.

The foregoing detailed description is given for clearness of understanding only, and no unnecessary limitations should be understood therefrom, as modifications will be obvious to those skilled in the art.

We claim:

1. A single electrode assembly for cardiac output or other hemodynamic parameters output monitoring, comprising:
   a first pair of electrodes consisting of a first spot injection electrode adapted to be placed adjacent the xiphoid process with a backing and means, including a relatively small conductive strip on the backing, for injecting a first signal into the patient's body at the xiphoid process and
   a first elongated strip electrode adapted to be placed adjacent the xiphoid process with means, including an elongated first backing and an elongated conductive strip on the elongated first backing, for sensing the first signal when received at the xiphoid process; and
   a second pair of electrodes consisting of a second spot electrode adapted to be placed adjacent the neck with means, including a backing and a small conductive strip on the backing, for injection of a second signal into the patient's body at the neck, and
   a second elongated strip electrode adapted to be placed adjacent the neck with means, including an elongated second backing and an elongated conductive strip on the elongated second backing, for sensing the second signal when received at the neck; and
   a single connector assembly including a plurality of leads respectively connected to all the above electrodes at one end and commonly connected to a single connector at the other end and cable means attached to the connector for coupling both pairs of the electrodes to a monitoring apparatus.

2. The electrode assembly of claim 1 in which the backing of the first spot electrode is separate from the backing of the first elongated electrode to facilitate different selected spacings between the electrodes for different patients.

3. The electrode assembly of claim 2 in which the first spot electrode is substantially smaller in area than the first elongated strip electrode.

4. The electrode assembly of claim 1 in which the backing of the second spot electrode is separate from the backing of the second elongated electrode to facilitate different selected spacings between electrodes.

5. The electrode assembly of claim 4 in which the second spot electrode is substantially smaller in area than the second elongated electrode.

6. In a method of cardiac output or other hemodynamic parameters monitoring including the step of analyzing signals from electrodes applied to a patient's body, the improvement comprising the steps of:
   placing a first spot injection electrode adjacent the neck of a patient;
   placing a first measuring strip electrode adjacent the neck of the patient which has a substantially greater surface area than that of the first spot electrode;
   injecting a first signal into the patient's body only via the first spot injection electrode;
   sensing the first signal as received at the first measuring electrode;
   placing a second spot electrode adjacent the xiphoid process of the patient;
   placing a second measuring strip electrode adjacent the xiphoid process of the patient and the second spot electrode;
   injecting a second signal into the patient's body via the second spot electrode; and
   sensing the second signal as received at the second measuring electrode.

* * * * *

DEVICE FOR CARDIAC OUTPUT MONITORING

This application is a continuation of application Ser. No. 06/786,445, filed Oct. 11, 1985 now abandoned, which is a continuation of application Ser. No. 586,612, filed Mar. 6, 1984, now abandoned.

BACKGROUND OF THE INVENTION

The present invention relates to cardiac output monitors or other hemodynamic parameters.

An assortment of electrodes have been known in the past for ECG monitoring of a patient's body. However, it is now desirable to perform cardiac output monitoring or other hemodynamic parameters in which a high frequency signal is injected into the patient's body and the signal is sensed to measure impedance. It is necessary to devise special electrodes for this procedure. These electrodes should be larger in area than present electrodes in order to limit the skin impedance to a lower level, thus minimizing noise and artifacts to the impedance amplifier resulting in low but stable electrode-to-skin impedance.

SUMMARY OF THE INVENTION

A principal feature of the present invention is the provision of a device for cardiac output monitoring or other hemodynamic parameters.

The device of the present invention comprises, a first electrode for placement adjacent the neck comprising, an elongated first backing, a first elongated conductive strip on the backing, and a second elongated conductive strip on the backing. The device has a second electrode for placement adjacent the xiphoid process comprising, a second elongated backing, a first elongated conductive strip on the second backing, and a second elongated conductive strip on the second backing.

A feature of the present invention is that the first strip of the first electrode is utilized to input a signal into the patient's body.

Another feature of the invention is that the second strip of the first electrode is utilized to sense the signal.

Yet another feature of the invention is that the first strip of the second electrode is utilized to input the signal into the patient's body.

Still another feature of the invention is that the second strip of the second electrode is utilized to sense the signal.

A feature of the present invention is that the electrodes are larger in area than present electrodes in order to limit the skin impedance to a lower level for these inherently low signal-to-noise measurements.

Another feature of the invention is that the electrodes minimize noise and artifacts to an impedance amplifier resulting in low but stable electrode-to-skin impedance.

These and other features and advantages are obtained at least in part through provision of a preferred embodiment of an electrode assembly for cardiac output or other hemodynamic parameters output monitoring in which two pairs of electrodes employ a single connector for connecting all electrodes to a monitor and in which each pair of electrodes consists of a single spot electrode for injection of a signal which is received by a single strip electrode. In one pair, a first spot injection electrode and strip reception electrode are placed adjacent the xiphoid process. In the second pair, a second spot injection electrode and a strip reception electrode are placed adjacent the neck.

Further features will become more fully apparent in the following description of the embodiments of this invention and from the appended claims.

DESCRIPTION OF THE DRAWINGS

In the drawings:

FIG. 1 is a perspective view of a cardiac output monitor of the present invention;

FIG. 2 is a plan view of electrodes for the monitor of FIG. 1;

FIG. 3 is another embodiment of the cardiac output monitor of the present invention; and FIG. 4 is a plan view of electrodes for the monitor of FIG. 3.

DESCRIPTION OF THE PREFERRED EMBODIMENTS

Referring now to FIGS. 1 and 2, there is shown a cardiac output monitor or other hemodynamic parameters generally designated 10 having a first electrode 12 for placement adjacent the neck of a patient, and a second electrode 14 for placement adjacent the xiphoid process of the patient.

The first electrode 12 has an elongated first backing 16, such as foam. The first electrode 12 has a first elongated conductive strip 18 on the backing 16, and a second elongated conductive strip 20 on the backing 16, with the first strip 18 being spaced from the second strip 20. The first electrode 12 has a pair of conductive leads 22 connected to the strips 18 and 20. The first electrode 12 may have adhesive 24 surrounding the strips 18 and 20 in order to secure the first electrode 12 to the patient's body. The conductive strips 18 and 20 may be constructed from an aluminized mylar, a conductive gel, or a conductive adhesive, as desired.

The second electrode 14 has a second elongated backing 26, such as foam. The second electrode 14 has a first elongated conductive strip 28 on the backing 26, and a second elongated conductive strip 30 on the backing 26, with the strip 28 being spaced from the strip 30. The second electrode 14 has a pair of conductive leads 32 connected to the first and second strips 28 and 30. The second electrode 14 also has an adhesive 34 surrounding the strips 28 and 30 in order to secure the second electrode 14 to the patient's body. The strips 28 and 30 may be constructed from an aluminized mylar, a conductive gel, or a conductive adhesive, as desired.

In use, the first electrode 12 is secured adjacent the patient's neck. A high frequency signal is injected into the patient's body on the first strip 18, and the signal is sensed on the second strip 20 to measure impedance. The leads 22 of the first electrode 12 are connected to a connector 36, which in turn is connected by conductive leads 38 to a suitable monitor. The second electrode 14 is secured to the patient's body adjacent the xiphoid process. The high frequency signal is also injected on the first strip 28, and the signal is sensed on the second strip 30 in order to measure impedance. The leads 32 of the second electrode 14 are connected to the connector 36, which is connected to the monitor over leads 38.

Another embodiment of the present invention is illustrated in FIGS. 3 and 4, in which like reference numerals designate like parts. In this embodiment, the monitor 10 has a first spot electrode 40 for placement adjacent the xiphoid process of the patient, a first elongated electrode 42 for placement adjacent the xiphoid process, a second spot electrode 44 for placement adjacent